(12) United States Patent
Yasuda et al.

(10) Patent No.: US 8,202,720 B2
(45) Date of Patent: Jun. 19, 2012

(54) MODEL CELL CHIP, APPARATUS FOR EVALUATING DRUG EFFECT USING THE MODEL CELL CHIP AND METHOD OF EVALUATING DRUG EFFECT

(75) Inventors: Kenji Yasuda, Tokyo (JP); Atsushi Sugiyama, Fuefuki (JP); Kentaro Ando, Yachiyo (JP); Fumimasa Nomura, Tokyo (JP); Hideyuki Terazono, Tokyo (JP); Tomoyuki Kaneko, Mitaka (JP); Mamoru Fukushima, Hachioji (JP)

(73) Assignees: Mitsubishi Chemical Medience Corporation, Tokyo (JP); National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 12/663,468

(22) PCT Filed: Jun. 6, 2008

(86) PCT No.: PCT/JP2008/060448
§ 371 (c)(1),
(2), (4) Date: Feb. 19, 2010

(87) PCT Pub. No.: WO2008/152983
PCT Pub. Date: Dec. 18, 2008

(65) Prior Publication Data
US 2010/0178692 A1 Jul. 15, 2010

(30) Foreign Application Priority Data

Jun. 8, 2007 (JP) .................................. 2007-152696
Jun. 8, 2007 (JP) .................................. 2007-152711

(51) Int. Cl.
*C12M 1/34* (2006.01)
*C12M 3/00* (2006.01)
*C12N 5/071* (2010.01)
*A61K 35/34* (2006.01)

(52) U.S. Cl. ................ 435/288.7; 435/286.1; 435/287.1; 435/366; 422/569

(58) Field of Classification Search ............... 435/288.7, 435/286.1, 287.1, 366; 424/569
See application file for complete search history.

(56) References Cited

U.S. PATENT DOCUMENTS
5,162,204 A * 11/1992 Matsuzaki et al. .............. 435/29
(Continued)

FOREIGN PATENT DOCUMENTS
JP 2006-094703 A 4/2006
(Continued)

OTHER PUBLICATIONS
English translation of Okano et al. (JP 2006-094703).*
(Continued)

*Primary Examiner* — Nathan Bowers
*Assistant Examiner* — Gautam Prakash
(74) *Attorney, Agent, or Firm* — Sughrue Mion, PLLC

(57) ABSTRACT

The present invention provides an apparatus for evaluating a drug effect enabling on-chip evaluation of the effect of a drug while the drug is acting on hERG-expressing cells. The present invention also provides a myocardial toxicity test apparatus and method therefor enabling in vitro myocardial toxicity testing that has previously been performed in vivo. A pulsating cell population and hERG-expressing cells (target model cells) are suitably isolated and arranged on a transparent substrate so that the two form gap junctions. The hERG-expressing cells are arranged on transparent electrodes provided on the transparent substrate. The hERG-expressing cells are exposed to a flow of a liquid containing a drug such that the drug acts thereon. The difference between the normal pulsation of hERG-expressing cells and the pulsation when a drug is acting thereon is captured via electric signals obtained from electrodes, and the properties of the change in potential are evaluated.

8 Claims, 8 Drawing Sheets

U.S. PATENT DOCUMENTS

2004/0106095 A1    6/2004    Thomson et al.
2007/0059763 A1    3/2007    Okano et al.

FOREIGN PATENT DOCUMENTS

| | | |
|---|---|---|
| JP | 2006-112846 A | 4/2006 |
| JP | 2006-115723 A | 5/2006 |
| WO | 2005/098425 A1 | 10/2005 |

OTHER PUBLICATIONS

Ikurou Suzuki, et al., "Detection of tetanus-induced effects in linearly lined-up micropatterned neuronal networks: Application of a multi-electrode array chip combined with agarose microstructures", Biochemical and Biophysical Research Communications, vol. 356, pp. 470-475, 2007.

Kenji Yasuda, "Efforts for the Constitutive Understanding of a Cell Network Constructed Atop an Agarose Microfabricated Chip", Chemistry & Chemical Industry, vol. 58, No. 2, pp. 144-146, Feb. 1, 2005. English translation.

Motohiko Chachin, et al., "Detection Method of Arrhythmogenic Drug Activity Using the HERG Channel Expression System", Folia Pharmacologica Japonica, vol. 119, No. 6, pp. 345-351, 2002. English translation.

Tomoyuki Kaneko, et al., "Dependence of the community effect of cultured cardiomyocytes on the cell network pattern", Biochemical and Biophysical Research Communications, vol. 356, pp. 494-498, 2007.

Extended European Search Report issued in EP 08765261.6 on Jul. 29, 2010.

Hirokazu Kaji et al., "Pharmacological characterization of micropatterned cardiac myocytes", Biomaterials, 2003, 24: 4239-4244.

Norbert Klauke et al., "Extracellular Recordings of Field Potentials from Single Cardiomyocytes", Biophysical Journal, 2006, 91: 2543-2551.

Matt Deacon et al., "Early evaluation of compound QT prolongation effects: A predictive 384-well fluorescence polarization binding assay for measuring hERG blockade", Journal of Pharmacological and Toxicological Methods, 2007, 55: 255-264.

Peter Hoffmann et al., "Are hERG channel inhibition and QT interval prolongation all there is in drug-induced torsadogenesis? A review of emerging trends", Journal of Pharmacological and Toxicological Methods, 2006, 53: 87-105.

Kensuke Kojima et al., "A novel method of cultivating cardiac myocytes in agarose microchamber chips for studying cell synchronization", Journal of Nanobiotechnology, 2004, 2(9): 1-4.

\* cited by examiner (a)

(b)

(c)

(d)

(a) PULSATION OF CELL POPULATION (b) PULSATION OF TARGET CELLS
(NORMAL STATE)

(c) PULSATION OF TARGET CELLS
(NORMAL STATE)

(a) CHANGE IN VOLUME OF CELLS DUE TO PULSATION OF CELL POPULATION (b) CHANGE IN VOLUME OF CELLS DUE TO PULSATION OF TARGET CELLS (NORMAL)

(c) CHANGE IN VOLUME OF CELLS DUE TO PULSATION OF TARGET CELLS (DRUG ACTING)

MODEL CELL CHIP, APPARATUS FOR EVALUATING DRUG EFFECT USING THE MODEL CELL CHIP AND METHOD OF EVALUATING DRUG EFFECT

TECHNICAL FIELD

The present invention relates to a model cell chip, an apparatus for evaluating a drug effect using the model cell chip, and a method of evaluating the drug effect. More particularly, the present invention relates to a model cell chip utilizing hERG-expressing cells, an apparatus for evaluating a drug effect using the model cell chip, a myocardial toxicity test apparatus for testing myocardial toxicity of a drug by using cardiomyocytes, a myocardial toxicity test chip, and a myocardial toxicity test method.

BACKGROUND ART

Bioassays are widely used to observe changes in the status of cells and the response of cells to a drug, etc. In general, cultured cells have been frequently used in conventional bioassays. Because assays in such a system are carried out using a plurality of cells, an average value from a population of cells has been viewed as if it were the property of a single cell.

Actually it is rare, however, for the cell cycle to be synchronized within a population, and cells express their proteins at different points in the cell cycle. Therefore, every analysis of response to a stimulus is always accompanied by the problem of fluctuation.

In other words, because the universal responses of cellular reaction mechanisms themselves fluctuate, only averages of the responses can be obtained. Methods of synchronized culturing, etc., have been developed to solve these problems. However, using groups of cells that are always at the same stage means that such cells must be supplied continuously, and that has been a hindrance to the widespread acceptance and use of bioassays.

Moreover, there are two types of stimuli (signals) to cells, i.e., ones provided by the amounts of signal substances, nutrients, and dissolved gases in the solution surrounding the cells, and ones caused by physical contact and intercellular interactions with other cells. As a result, these fluctuations have been difficult to evaluate.

The problems of physical contact and intercellular interactions can be solved to a certain extent by carrying out the bioassay with a cluster of cells such as a tissue fragment. Unlike cultured cells, however, cell clusters with uniform features cannot always be obtained in such a case. Thus, there is a problem because the resulting data is scattered, and information gets buried within the population.

As disclosed in Japanese Patent Application Laid-open No. 2006-94703 (Patent Document 1), the inventors of the present application have proposed a cell aggregate microarray (bioassay chip) with a structure constituting a plurality of cell culturing compartments for enclosing the cells in a specific spatial configuration, having adjacent compartments mutually linked by grooves or tunnels too narrow for a cell to pass therethrough, and as needed, having in the grooves, tunnels, or cell culturing compartments a pattern of a plurality of electrodes for measuring changes in cell action potential in order to carry out measurements by a data processing model using each individual cell in a group of cells as the minimum structural unit thereof.

Patent document 1: Japanese Patent Application Laid-open No. 2006-94703

In conventional bioassays, either cells have been treated as a tissue fragment, or cultured cells have been treated as a single cell. As noted in the aforementioned discussion of background art, there is a problem when the number of cells becomes too large because the resulting data becomes an average value, and the response to a drug, etc., cannot be accurately ascertained therefrom. Whenever cells are used one by one, however, cells that originally function as cells of a multicellular tissue are used as cells in an isolated, independent state. As a result, the effects of intercellular interactions no longer appear, and as can be expected, there is a problem in accurately obtaining a response to a drug, i.e., the bioassay data.

When evaluating the effect of a drug on a cell, it is important to develop a device and system wherein cell potential and cell morphology can be measured accurately on a single cell basis, and wherein a cytotoxicity test can be measured accurately in the form of cell potential and cell morphology on a single cell basis.

Additionally, as for cardiomyocytes and fibroblasts, it is important to develop a device and system wherein the propagation of a pulse wave from an adjacent cardiomyocyte or fibroblast can be measured accurately on a single cell basis in terms of cell morphology and cell potential, and wherein a test for toxicity of a drug on a cardiomyocyte can be accurately performed by measurements of cell potential and cell morphology on a single cell basis.

DISCLOSURE OF THE INVENTION

The present invention provides a model cell chip, apparatus for evaluating a drug using the model cell chip, and a method for evaluating a drug that comprises evaluating a drug effect by the model cell chip described below.

(1) A model cell chip comprising:
   a substrate;
   a plurality of cell holders each holding a cell of a population of cardiomyocytes which comprise a plurality of cells arranged on the substrate and pulsating stably;
   a cell holder holding an hERG-expressing cell capable of communicating with a single cell of the cell population and transmitting the pulse of the cell population;
   a wall formed on the substrate for filling in with a liquid culture medium around the cell population and the hERG-expressing cell;
   a microelectrode which is provided on the substrate, and on which a single cell of the cell population is to be arranged;
   a microelectrode which is provided on the substrate, and on which the hERG-expressing cell is to be arranged;
   a reference electrode placed in the area enclosed by the wall; and
   a leading line connected to each of the microelectrodes and a leading line connected to the reference electrode.

(2) The model cell chip described in (1) above, wherein a barrier is provided between an area in which the plurality of cell holders each holding a cell of the cell population are formed and an area in which the cell holder of the hERG-expressing cell is positioned, so as to impede the flow of the liquid culture medium, the barrier having an opening for making a single cell of the cell population communicate with the hERG-expressing cells.

(3) The model cell chip described in (1) above, wherein the cell holders are enclosed by walls that are non-adhesive to cells and have gaps too narrow for a cell to pass therethrough.

(4) An apparatus for evaluating a drug effect using a model cell chip comprising:
  a substrate;
  cell holders that hold a cell population comprising a plurality of stably pulsating cardiomyocytes arranged on the substrate;
  a cell holder that holds an hERG-expressing cell capable of communicating with a single cell of the cell population and transmitting the pulse of the cell population;
  a wall formed on the substrate for filling with a liquid culture medium around the cell population and the hERG-expressing cell;
  a microelectrode which is provided on the substrate, and on which a single cell of the cell population is to be arranged;
  a microelectrode which is provided on the substrate, and on which the hERG-expressing cell is to be arranged;
  a reference electrode placed in the area enclosed by the wall;
  a leading line connected to each of the microelectrodes and a leading line connected to the reference electrode;
  a liquid culture medium supply and withdrawal means whereby the liquid culture medium is supplied to and withdrawn from the area enclosed by the wall;
  means for adding a drug acting on the cells to the liquid culture medium; and
  means for measuring and recording the potentials of cells arranged on the microelectrodes using the leading line connected to each of the microelectrodes and the leading line connected to the reference electrode.
(5) The apparatus for evaluating a drug effect using the model cell chip described in (4) above, wherein a barrier is provided between an area in which the cell population is formed and an area in which the hERG-expressing cell is positioned so as to impede the flow of the liquid culture medium, the barrier having an opening for making a single cell of the cell population communicate with the hERG-expressing cell.
(6) The apparatus for evaluating a drug effect using the model cell chip described in (4) above, wherein the cell holders are enclosed by walls that are non-adhesive to cells and have gaps too narrow for a cell to pass therethrough.
(7) The apparatus for evaluating a drug effect using the model cell chip described in (4) above, wherein the liquid culture medium supply means for supplying the liquid culture medium is combined with the means for adding a drug acting on the cells.
(8) A method for evaluating the effect of a drug acting on the cells using a model cell chip that utilizes the apparatus for evaluating a drug effect using a model cell chip comprising:
  a substrate;
  cell holders that hold a cell population comprising a plurality of stably pulsating cardiomyocytes arranged on the substrate;
  a cell holder that holds an hERG-expressing cell capable of communicating with a single cell of the cell population and transmitting the pulse of the cell population;
  a wall formed on the substrate for filling with a liquid culture medium around the cell population and the hERG-expressing cells;
  a microelectrode which is prepared on the substrate, and on which a single cell of the cell population is to be arranged;
  a microelectrode which is prepared on the substrate, and on which the hERG-expressing cell is to be arranged;
  a reference electrode placed in the area enclosed by the wall;
  a leading line connected to each of the microelectrodes and a leading line connected to the reference electrode;
  liquid culture medium supply and withdrawal means whereby the liquid culture medium is supplied to and withdrawn from the area enclosed by the wall;
  means for adding a drug acting on the cells to the liquid culture medium; and
  means for measuring and recording the potentials of cells arranged on the microelectrodes using the leading line connected to each of the microelectrodes and the leading line connected to the reference electrode,
  and that includes a step of evaluating whether or not the pulse generated by the cell population decreases the amplitude of the electric signal generated by the hERG-expressing cell when the drug acting on the cells is added to the liquid culture medium.
(9) A model cell chip comprising:
  a substrate;
  a cardiomyocyte population holding area that includes a plurality of cell holders each holding a cell of a cell population comprising a plurality of stably pulsating cardiomyocytes arranged on the substrate;
  an hERG-expressing cell holding area that includes a cell holder holding an hERG-expressing cell capable of communicating with a single cell of the cell population and transmitting the pulse of the cell population;
  an area that is to be filled with liquid culture medium and defined by the surface of the substrate and a wall formed around the perimeter of the cardiomyocyte population holding area and the hERG-expressing cell holding area;
  a microelectrode which is placed in one of the cell holders in the cardiomyocyte population holding area on the substrate, and on which a cardiomyocyte is to be arranged;
  a microelectrode which is placed in one of the cell holders of the hERG-expressing cell holding area on the substrate, and on which the hERG-expressing cell is to be arranged;
  a reference electrode placed in the area to be filled in with the liquid culture medium; and
  a leading line connected to each of the microelectrodes and a leading line connected to the reference electrode.
(10) An apparatus for evaluating a drug using a model cell chip comprising:
  a substrate;
  a cardiomyocyte population holding area that includes a plurality of cell holders each holding a cell of a cell population comprising a plurality of stably pulsating cardiomyocytes arranged on the substrate;
  an hERG-expressing cell holding area that includes a cell holder holding an hERG-expressing cell capable of communicating with a single cell of the cell population and transmitting the pulse of the cell population;
  an area that is to be filled in with liquid culture medium and defined by the surface of the substrate and a wall formed around the perimeter of the cardiomyocyte population holding area and the hERG-expressing cell holding area;
  a microelectrode which is placed in one of the cell holders of the cardiomyocyte population holding area on the substrate, and on which a cardiomyocyte is to be arranged;
  a microelectrode which is placed in one of the cell holders in the hERG-expressing cell holding area on the substrate, and on which the hERG-expressing cell is to be arranged;
  a reference electrode placed in the area to be filled in with the liquid culture medium;

a leading line connected to each of the microelectrodes and a leading line connected to the reference electrode;

liquid culture medium supply and withdrawal means whereby the liquid culture medium is supplied to and withdrawn from the area to be filled in with liquid culture medium;

liquid culture medium supply means for adding a drug acting on the hERG-expressing cell to the liquid culture medium; and means for measuring and recording the potentials of cells arranged on the microelectrodes using the leading line connected to each of the microelectrodes and the leading line connected to the reference electrode.

(11) A method for evaluating a drug effect that utilizes the apparatus for evaluating a drug effect using a model cell chip described in (10) above, and includes a step of using a model cell chip to evaluate the drug effect of a drug acting on the hERG-expressing cell by evaluating the decrease in amplitude of the electric signal generated by the hERG-expressing cell based on the pulse generated by the cardiomyocyte population when the drug acting in the hERG-expressing cell is added to the liquid culture medium.

The present invention uses a structure in which a single cell is contained in a specific spatial configuration, and it features a suitably sized, controlled cardiomyocyte population that functions as a pacemaker producing a stable pulse. In addition, the present invention features a cell holder adjacent thereto containing only a single hERG-expressing cell that interacts with this cell population. In the presence of a normal liquid culture medium the pulse generated by the cardiomyocyte population is propagated to the hERG-expressing cell. The status of this propagation is measured by measuring the respective cell potentials of the electrode provided to a single cardiomyocyte of the cardiomyocyte population and the electrode provided to the hERG-expressing cell.

Then, measurement and detection are carried out in the manner in the presence of a liquid culture medium to which a drug acting on the hERG-expressing cell has been added, and the toxicity of the drug to the hERG-expressing cell is evaluated by comparing the measurements and detection results of the two cases.

The present invention also provides the following myocardial toxicity test apparatus, myocardial toxicity test chip, and myocardial toxicity test method.

(1) A myocardial toxicity test apparatus having:
a transparent substrate;
a cell population pulsating stably, containing cardiomyocytes and comprising a plurality of cells arranged on the transparent substrate;
a cell communication channel including a plurality of cardiomyocytes and fibroblasts arranged in tandem that are in communication with a single cell of the cell population and that transmit the pulse of the cell population;
a wall formed on the transparent substrate for filling in a liquid culture medium around the periphery of the cell population and the cell communication channel;
liquid culture medium supply and withdrawal means whereby the liquid culture medium is supplied to and withdrawn from the area enclosed by the wall;
means for adding a drug acting on the cells to the liquid culture medium;
a microelectrode which is provided on the transparent substrate, and on which a single cell of the cell population is to be arranged;
a plurality of separate microelectrodes, which are provided on the transparent substrate, and on which each of the several respective cells of the cell communication channel is to be arranged;
a reference electrode placed in the area enclosed by the wall;
means for measuring and recording the potentials of cells arranged on the microelectrodes using a leading line connected to each of the microelectrodes and the leading line connected to the reference electrode; and
means for optically measuring the state of a single cell arranged on the transparent substrate.

(2) The myocardial toxicity test apparatus described in (1) above, wherein the cell is enclosed by walls that are non-adhesive to the cell and have gaps such that the cell cannot pass through.

(3) The myocardial toxicity test apparatus described in (1) above, wherein a barrier is provided between the area in which the cell population is formed and the area in which the cell communication channel is formed to impede the flow of the cell culture medium, the barrier having an opening for making a single cell of the cell population communicate with the cell on the end of the cell communication channel.

(4) The myocardial toxicity test apparatus described in (1) above, wherein means for adding a drug acting on the cells is attached to a liquid culture medium circulation means that circulates the liquid culture medium.

(5) A myocardial toxicity test apparatus having:
a transparent substrate;
a cell population including a plurality of cells arranged on the transparent substrate;
a cell communication channel including a plurality of cardiomyocytes and fibroblasts arranged in tandem that are in communication with a single cell of the cell population and that transmit the pulse of the cell population;
a wall formed on the transparent substrate for filling in liquid culture medium around the periphery of the cell population and the cell communication channel;
liquid culture medium supply and withdrawal means whereby the liquid culture medium is supplied to and withdrawn from the area enclosed by the wall;
means for adding a drug acting on the cells to the liquid culture medium;
a microelectrode, which is provided on the transparent substrate, and on which a single cell of the cell population is to be arranged;
a plurality of separate microelectrodes which are provided on the transparent substrate, and on which each of the several respective cells of the cell communication channel is to be arranged;
a reference electrode placed in the area enclosed by the wall;
means for measuring and recording the potentials of cells arranged on the microelectrodes using a leading line connected to each of the microelectrodes and the leading line connected to the reference electrode;
a stage which can be moved in the X-Y direction, and on which the transparent substrate is to be arranged; and
means for optically measuring the state of a cell on the transparent substrate that is mounted on the stage.

(6) The myocardial toxicity test apparatus described in (5) above, wherein the cell is enclosed by walls that are non-adhesive to the cell and have gaps too narrow for the cell to pass therethrough.

(7) The myocardial toxicity test apparatus described in (5) above, wherein a barrier is provided between an area formed by the cell population and an area formed by the cell communication channel in order to impede the flow of the liquid culture medium, the barrier having an opening for making a single cell on the end of the cell communication channel communicate with the hERG-expressing cells.

(8) The myocardial toxicity test apparatus described in (5) above, wherein means for adding a drug acting on the cells is attached to the liquid culture medium supply means.

(9) A myocardial toxicity test chip comprising:
- a transparent substrate;
- a cell population comprising a plurality of cells arranged on the transparent substrate;
- a cell communication channel including a plurality of cardiomyocytes and fibroblasts arranged in tandem that are in communication with a single cell of the cell population and that transmit the pulse of the cell population;
- a wall formed on the transparent substrate for filling in a liquid culture medium around the periphery of the cell population and the cell communication channel;
- a microelectrode which is provided on the transparent substrate, and on which a single cell of the cell population is to be arranged;
- a plurality of separate microelectrodes which are provided on the transparent substrate, and on which each of the several respective cells of the cell communication channel is to be arranged;
- a reference electrode placed in the area enclosed by the wall; and
- a leading line connected to each of the microelectrodes and a leading line connected to the reference electrode.

(10) The myocardial toxicity test chip described in (9) above, wherein the cell is enclosed by walls that are non-adhesive to the cell and have gaps too narrow for the cell to pass therethrough.

(11) The myocardial toxicity test chip described in (9) above having an opening between the area in which the cell population is formed and the area in which the cell communication channel is formed in order to impede the flow of the cell culture medium, and for making a single cell of the cell population communicate with the cell on the end of the cell communication channel.

(12) A myocardial toxicity test method using a myocardial toxicity test apparatus,
the apparatus comprising:
- a transparent substrate;
- a cell population comprising a plurality of cells arranged on the transparent substrate;
- a cell communication channel including a plurality of cardiomyocytes and fibroblasts arranged in tandem that are in communication with a single cell of the cell population and that transmit the pulse of the cell population;
- a wall formed on the transparent substrate for filling in a liquid culture medium around the periphery of the cell population and the cell communication channel;
- liquid culture medium supply and withdrawal means whereby the liquid culture medium is supplied to and withdrawn from the area enclosed by the wall;
- means for adding a drug acting on the cells to the liquid culture medium;
- a microelectrode which is provided on the transparent substrate, and on which a single cell of the cell population is to be arranged;
- a plurality of separate microelectrodes which are provided on the transparent substrate, and on which each of the several respective cells of the cell communication channel is to be arranged;
- a reference electrode placed in the area enclosed by the wall;
- means for measuring and recording the potentials of cells arranged on the microelectrodes using a leading line connected to each of the microelectrodes and the leading line connected to the reference electrode; and
- means for optically measuring the state of a cell arranged on the transparent substrate, and
said method comprising:
- evaluating whether or not there is a time lag in the speed at which the pulse generated by the cell population is transmitted via the cell communication channel when a drug acting on the cells has been added to the liquid culture medium so as to test the myocardial toxicity of a drug acting on the cells.

(13) A myocardial toxicity test apparatus comprising:
- a transparent substrate;
- a cardiomyocyte population holding area configured on the transparent substrate and comprising a plurality of cell holders ($CH_G$) for holding stably pulsating cardiomyocytes;
- a cell communication channel including a plurality of cell holders ($CH_n$) arranged in tandem for communicating with a single cell of the cell holders and for transmitting the pulse of the cardiomyocyte population, wherein the cell holders ($CH_n$) thereof hold cardiomyocytes and fibroblasts;
- an area which is to be filled in with liquid culture medium and defined by the surface of the transparent substrate and a wall formed around the perimeter of the cardiomyocyte population holding area and the cell communication channel;
- liquid culture medium supply and withdrawal means for supplying and withdrawing the liquid culture medium to and from the area enclosed by the wall;
- drug supply means for adding a drug acting on the cells to the liquid culture medium;
- a microelectrode which is placed in a single cell holder ($CH_G$) in the cardiomyocyte population holding area on the transparent substrate, and on which a cardiomyocyte is to be arranged;
- a plurality of microelectrodes which are placed in the plurality of cell holders ($CH_n$) of the cell communication channel on the transparent substrate, and on which the cardiomyocytes or fibroblasts are to be arranged;
- a reference electrode placed in the area enclosed by the wall;
- means for measuring and recording the potentials of cells arranged on the microelectrodes using a leading line connected to each of the microelectrodes and the leading line connected to the reference electrode; and
- means for optically measuring the state of a cell arranged on the transparent substrate.

(14) The myocardial toxicity test apparatus described in (13) above, wherein each of the cell holders ($CH_G$, $CH_n$) is defined as a space that is provided on the above transparent substrate and that is enclosed by walls that are non-adhesive to cells and have gaps too narrow for the cells to pass therethrough.

(15) The myocardial toxicity test apparatus described in (13) above, wherein a barrier is provided between the cardiomyocyte population holding area and the cell communication channel in order to impede the flow of the cell culture medium, the barrier having an opening for making a cell held in one of the plurality of cell holders ($CH_G$) in the cardiomyocyte population holding area communicate with the cell in the cell holder ($CH_n$) on the end of the cell communication channel.

(16) A myocardial toxicity test apparatus providing:
- a transparent substrate;
- a cardiomyocyte population holding area that includes a plurality of cell holders ($CH_G$) arranged on the transparent substrate;
- a cell communication channel including a plurality of cell holders ($CH_n$) arranged in tandem that communicates with a single cell of the cell holders ($CH_G$) of the cardiomyocyte population holding area and transmits the pulse of the cardiomyocyte population, wherein the cell holders ($CH_n$) hold cardiomyocytes and fibroblasts;
- an area which is to be filled in with liquid culture medium and defined by the surface of the transparent substrate and a wall formed around the perimeter of the cardiomyocyte population holding area and the cell communication channel;
- liquid culture medium supply and withdrawal means for supplying and withdrawing the liquid culture medium to and from the area enclosed by the wall;
- drug supply means for adding a drug acting on the cells to the liquid culture medium;
- a microelectrode which is placed in a single cell holder ($CH_G$) in the cardiomyocyte population holding area on the transparent substrate, and on which a cardiomyocyte is to be arranged;
- a plurality of microelectrodes which are placed in the plurality of cell holders ($CH_n$) of the cell communication channel on the transparent substrate, and on which the cardiomyocytes or fibroblasts are to be arranged;
- a reference electrode placed in the area enclosed by the wall;
- means for measuring and recording the potentials of cells arranged on the microelectrodes using a leading line connected to each of the microelectrodes and the leading line connected to the reference electrode;
- a stage which can be moved in the X-Y direction, and on which the transparent substrate is to be arranged; and
- means for optically measuring the state of a cell arranged on the transparent substrate arranged on the stage.

(17) A myocardial toxicity test chip providing:
- a transparent substrate,
- a cardiomyocyte population holding area configured on the transparent substrate and including a plurality of cell holders ($CH_G$) for holding the cardiomyocytes;
- a cell communication channel including a plurality of cell holders ($CH_n$) arranged in tandem for communicating with a single cell of the cardiomyocyte population and transmitting the pulse of the cardiomyocyte population, wherein the cell holders ($CH_n$) thereof hold cardiomyocytes and fibroblasts;
- an area which is to be filled in with liquid culture medium and defined by the surface of the transparent substrate and a wall formed around the perimeter of the cardiomyocyte population holding area and the cell communication channel;
- a microelectrode which is placed in a single cell holder ($CH_G$) in the cardiomyocyte population holding area on the transparent substrate, and on which a cardiomyocyte is to be arranged;
- a plurality of microelectrodes which are placed in the plurality of cell holders ($CH_n$) of the cell communication channel on the transparent substrate, and on which the cardiomyocytes or fibroblasts are to be arranged;
- a reference electrode placed in the area enclosed by the wall; and
- a leading line connected to each of the microelectrodes and a leading line connected to the reference electrode.

(18) A myocardial toxicity test method, comprising:
evaluating whether or not there is a time lag in the speed at which the pulse generated by the cell population is transmitted via the cell communication channel when a drug acting on the cells has been added to the liquid culture medium so as to test the myocardial toxicity of a drug acting on the cells using the myocardial toxicity test apparatus described in any of (13) to (16) above.

The present invention uses a structure in which a single cell is contained in a specific spatial configuration, and it features a suitably sized, controlled cardiomyocyte population that functions as a pacemaker producing a stable pulse. In addition the present population features a pulsating cell connection channel wherein a plurality of cardiomyocytes and fibroblasts interacting with the cell population are arranged in tandem. In the presence of normal liquid culture medium, the pulse generated by the cardiomyocyte population is propagated via the pulsating cell communication channel, i.e., the pulse is sequentially propagated by the cardiomyocytes and fibroblasts arranged in tandem. The state of propagation is measured by measuring the cell potential of the electrode provided to a single cardiomyocyte of the cardiomyocyte population and the electrodes provided to each of the cardiomyocytes and fibroblasts arranged in tandem. Additionally, the state of the pulsation of a cardiomyocyte among the pulsating cells arranged in tandem is detected optically.

Next, measurement and detection are carried out in the manner in the presence of a liquid culture medium to which a drug acting on cardiomyocytes has been added, and the toxicity of the drug to cardiomyocytes is evaluated by comparing the measurements and detection results of both.

The present invention enables the toxicity of a drug to hERG-expressing cells to be measured and evaluated accurately.

The present invention also enables the propagation of a pulse of cardiomyocytes and fibroblasts to be measured and evaluated accurately on a single cell basis using cell potential and optical data.

EXPLANATION OF REFERENCE NUMBERS

First Embodiment

Figure 1:
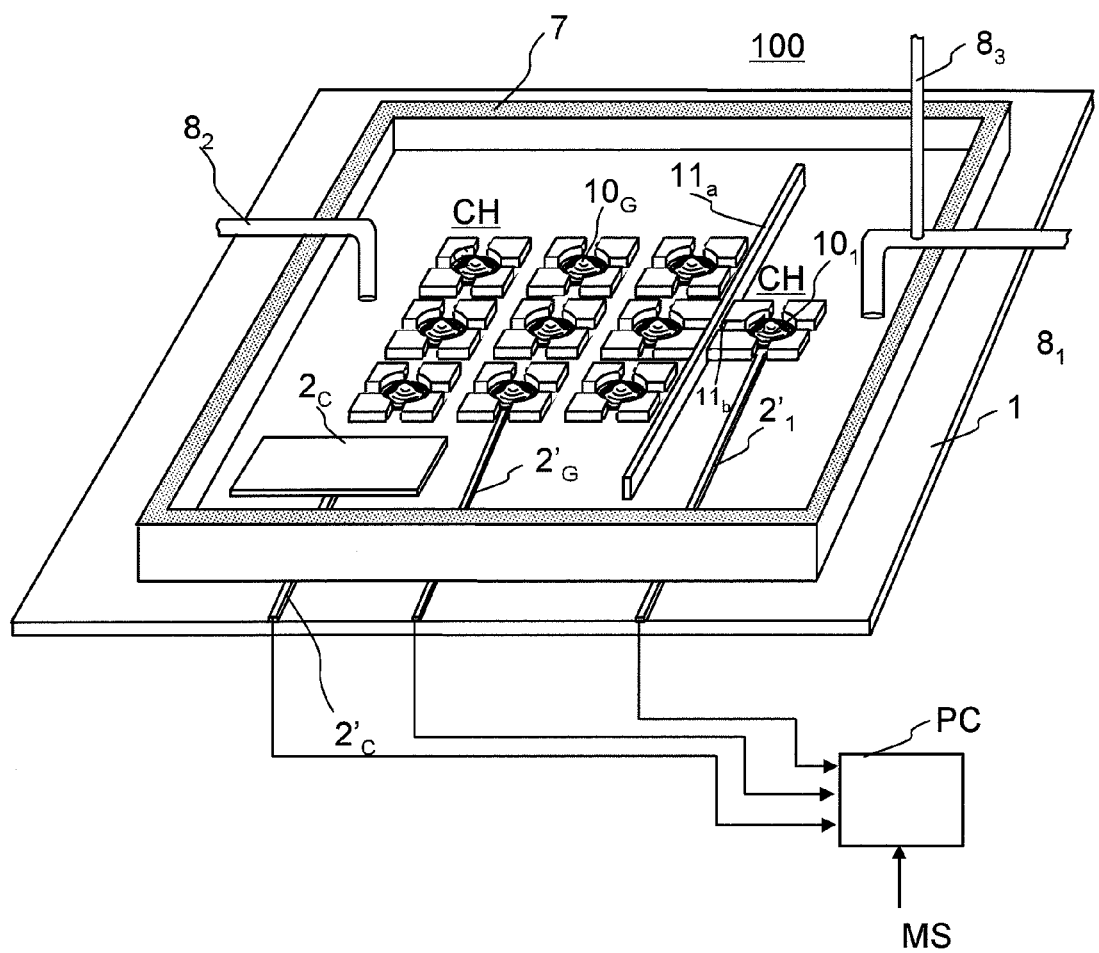
FIG. 1 is a perspective view schematically illustrating one example of the structure of the model cell chip and the apparatus for evaluating a drug effect using the model cell chip as in the first embodiment of the present invention.
Figure 2:
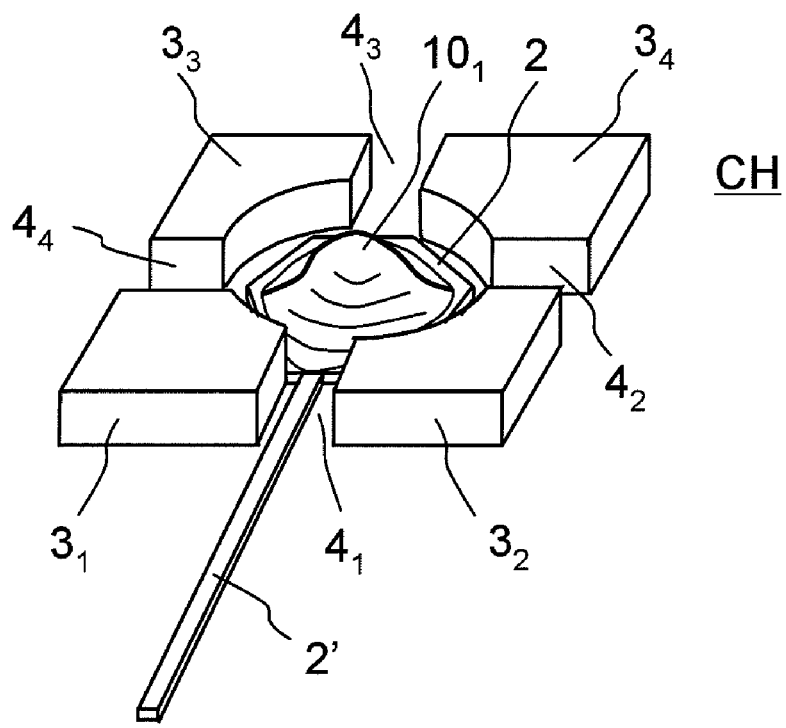
FIG. 2 is a perspective view schematically illustrating one example of the structure of the cell holder CH of the model cell chip and the apparatus for evaluating a drug effect using the model cell chip shown in FIG. 1.
Figure 3:
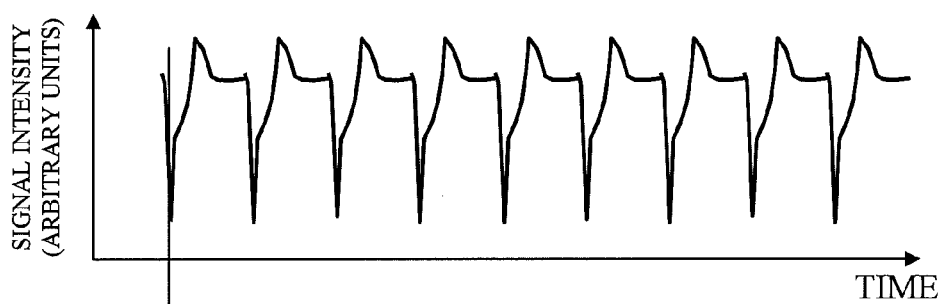
FIGS. 3(a), (b), (c) and (d) are graphs showing signals relating to the measurement of cell potential in the first embodiment of the present invention.
Figure 3:
Figure 3:
Figure 3:
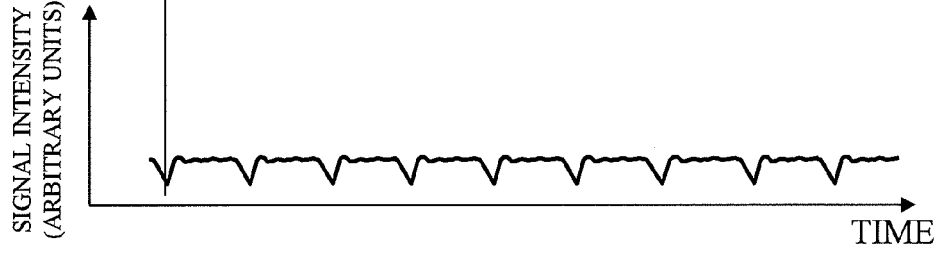

FIGS. 1 to 3

1: transparent substrate, 2: microelectrode, $2_C$: reference electrode, 2': leading line of microelectrode 2, $3_1$, $3_2$, $3_3$, and $3_4$: agarose gel walls, $4_1$, $4_2$, $4_3$, and $4_4$: gaps, 7: wall surrounding perimeter, $8_1$, $8_2$, and $8_3$: pipes, PC: personal computer, Ms: personal computer manipulation signal, $10_G$: cardiomyocyte, $CH_G$: cell population, $CH_1$: cell holder, $10_1$: hERG-expressing cell, $11_a$: barrier, $11_b$: opening, 100: apparatus for evaluating a drug effect using a model cell chip.

Second Embodiment

FIGS. 4 to 9

1: transparent substrate, 2: microelectrode, $2_C$: reference electrode, 2': leading line of microelectrode 2, $3_1$, $3_2$, $3_3$, and $3_4$: agarose gel walls, $4_1$, $4_2$, $4_3$, and $4_4$: gaps, 7: wall surrounding perimeter, $8_1$, $8_2$, $8_3$: pipes, PC: personal computer, Ms: personal computer manipulation signal, $10_0$, $10_1$, $10_2$, $10_3$, - - -, $10_n$: cardiomyocyte or fibroblast, 15: transparent stage of optical observation apparatus, 16: X-Y drive apparatus, 18: Z drive apparatus, $CH_1$, $CH_2$, $CH_3$, and $CH_n$: cell holders, CCC: cell communication channel, $10_G$: cell population, $11_a$: barrier, $11_b$: opening, 19: dichroic mirror, 20: bandpass filter, 21: camera, 22: light source, 23: bandpass filter, 24: shutter, 25: condenser, 26: objective lens, 100: myocardial toxicity test apparatus.

BEST MODE FOR CARRYING OUT THE INVENTION

FIG. 1 is a perspective view schematically illustrating one example of the structure of the model cell chip and the apparatus for evaluating a drug effect using the model cell chip according to the first embodiment of the present invention.

FIG. 2 is a perspective view schematically illustrating one example of the structure of the cell holder CH of the model cell chip and the apparatus for evaluating a drug effect using the model cell chip shown in FIG. 1.

In the figure, 100 is the apparatus for evaluating a drug effect using a model cell chip, which apparatus being constituted mainly by the parts configured on the transparent substrate 1. The transparent substrate 1 is an optically transparent material, for example a glass substrate or silicon substrate. The microelectrode 2 is, for example, an ITO transparent electrode, and is configured on the transparent substrate 1. The leading line 2' is a line for the microelectrode 2. There are walls formed of agarose gel $3_1$, $3_2$, $3_3$, and $3_4$ configured around the microelectrode 2 with gaps $4_1$, $4_2$, $4_3$, and $4_4$. The agarose gel walls $3_1$, $3_2$, $3_3$, and $3_4$ are cut out in the center to form a hollow space constituting a cell holder. As needed, a microelectrode 2 is configured on the transparent substrate 1 in the hollow space constituting the cell holder formed by the agarose gel walls $3_1$, $3_2$, $3_3$, and $3_4$. The cell holder can hold a single cell 10 regardless of the presence or absence of a microelectrode 2. In FIG. 2, a microelectrode 2 is configured on the transparent substrate 1 in the hollow space constituting the cell holder formed by the agarose gel walls $3_1$, $3_2$, $3_3$, and $3_4$, and a cardiomyocyte $10_1$ rests thereon. The figure shows a leading line 2' connected to and leading from the microelectrode 2. A substance to facilitate cell adhesion such as collagen can be applied to the cell holding surface when a cell is arranged directly on the cell holding surface of the microelectrode 2, or to the transparent substrate 1 that is provided without a microelectrode 2. With respect to the cell in the cell holder formed by the agarose gel walls $3_1$, $3_2$, $3_3$, and $3_4$, because the agarose gel is a non-adhesive surface to cells, the cell 10 cannot climb over the wall and migrate even if the height of the agarose gel walls $3_1$, $3_2$, $3_3$, and $3_4$ is about the same as the height of the cell. In addition, because the gaps $4_1$, $4_2$, $4_3$, and $4_4$ around the cell holder formed by cutting out the center of the agarose gel walls $3_1$, $3_2$, $3_3$, and $3_4$ are narrower than the size of a cell, the cell 10 cannot slip through the gaps $4_1$, $4_2$, $4_3$, and $4_4$.

In FIG. 1 a 3×3 array of cell holders CH is contained in the cardiomyocyte population holding area, and each cell holder CH holds a single cardiomyocyte $10_G$ in the cell holding member thereof. The cell population $CH_G$ constituted by the cardiomyocytes $10_G$ in the 3×3 array of cell holders CH functions as a pacemaker producing a stable pulse. A microelectrode 2 is provided to only one cell holder CH in the cell population $CH_G$, and a leading line $2'_G$ leads therefrom. An hERG-expressing cell $10_1$ is held in cell holder $CH_1$ that is positioned opposite the cell holder CH in the center of right side the cell population $CH_G$. The cell holder $CH_1$ is provided with a microelectrode 2, and the hERG-expressing cell $10_1$ is arranged on that microelectrode 2. A leading line $2'_1$ leads away from that microelectrode 2. A barrier $11_a$ is provided between the right side of the cell population $CH_G$ and the left edge of the cell holder $CH_1$ so that the hERG-expressing cell holding area containing cell holder $CH_1$, which holds hERG-expressing cell $10_1$, and the abovementioned cardiomyocyte population holding area are separated thereby. A small opening $11_b$ is formed in the bottom part of the center of the barrier $11_a$. The cell holder CH in the center of the right side of the cell population $CH_G$ and the cell holder $CH_1$ lie opposite each other on both sides of this opening $11_b$ and are configured to enable physical contact and intercellular interaction between the cells held in each respective cell holder via the gaps 4 surrounding each cell holder. A reference electrode $2_C$ is provided at the bottom of the cell population $CH_G$, and a leading line $2'_C$ leads therefrom.

Around the perimeter lies a wall 7 that encloses the cell population $CH_G$, the cell holder $CH_1$, and the reference electrode $2_C$. Pipes $8_1$ and $8_2$ are for supplying liquid culture medium to the area inside the wall 7 and for withdrawing liquid culture medium from the area inside the wall 7. In the example of this figure, the liquid culture medium is supplied via pipe $8_1$ that extends nearly to the bottom surface of the substrate 1, and the liquid culture medium is withdrawn via pipe $8_2$ that extends nearly to the bottom surface of the substrate 1. Pipe $8_3$ is connected near the liquid culture medium outlet of pipe $8_1$ that supplies the liquid culture medium, and the drug acting on the cells is supplied via pipe $8_3$. Therefore, the cell 10 is held stably on top of the microelectrode 2 while it is exposed to liquid culture medium supplied to the area inside the wall 7 via pipe $8_1$. When it is not necessary to expose the cells to liquid culture medium, the liquid culture medium can be withdrawn from the area inside the wall 7 via pipe $8_2$. In addition, when replacing the liquid culture medium with fresh medium, the fresh medium can be supplied either during or after withdrawal of the old culture medium. On the other hand, when exposing the cells to a drug, the drug acting on the cells can be added to the liquid culture medium via pipe $8_3$, and the liquid culture medium can then be supplied via pipe $8_1$ while withdrawing liquid culture medium via pipe $8_2$. At this time when liquid culture medium containing the drug is supplied to the area inside the wall 7 via pipe $8_1$, the effect of the drug on the cells of the cell population $CH_G$ will be less than the effect of the drug on the hERG-expressing cell of cell holder $CH_1$ because the barrier $11_a$ has been provided between the cell population $CH_G$ and the cell holder $CH_1$. In other words, when liquid culture medium containing the drug is supplied via pipe $8_1$, the liquid culture medium flows through the gaps between the wall 7 and both sides of the barrier $11_a$, and it also flows over the top of the barrier $11_a$, so the drug also affects the cells of the cell population $CH_G$ because it is provided to the cell population $CH_G$. However, because the effect on those cells is indirect in comparison with the effect on the hERG-expressing cell of cell holder $CH_1$, it is not great enough to affect their function as a pacemaker. The features and distribution of pipes $8_1$, $8_2$, and $8_3$ can be changed as desired in accordance with the method of measurement. For example, pipes $8_1$ and $8_3$ can be separated, or pipe $8_2$ can be omitted and pipe $8_1$ can be used for both supply and withdrawal.

In the figure, PC represents a personal computer that measures and records the cell potential between the leading line 2' of the microelectrode 2 of the cell holder CH and the leading line 2' of the reference electrode $2_C$. A manipulation signal Ms from an operator is sent to the personal computer 9.

Typical examples of the sizes of the structures of the apparatus for evaluating a drug effect using a model cell chip 100 illustrated in FIG. 1 are noted below. This example assumes a cell size of 10 μm in diameter. The size of the transparent substrate 1 is 100 mm×150 mm; the size of the microelectrode 2 is 8 μm×8 μm; the size of each of the agarose gel walls $3_1$, $3_2$, $3_3$, and $3_4$ is 20 μm×20 μm×10 μm (height); the width of the gaps $4_1$, $4_2$, $4_3$, and $4_4$ is 2 μm, the hollow space that is the cell holding member formed by the agarose gel walls $3_1$, $3_2$, $3_3$, and $3_4$ is a cylinder 12 μm in diameter; and the outside perimeter of the walls 7 is 5 mm×5 mm, and the height is also 5 mm. The height of the barrier $11_a$ is 1 mm. This case assumes that the microelectrode 2 is an 8 μm×8 μm square, but a round electrode with a 10 μm diameter to form the cell holding member constituted by all four agarose gel walls $3_1$, $3_2$, $3_3$, and $3_4$, and the width of the gaps $4_1$, $4_2$, $4_3$, and $4_4$ can also be used.

A structural example of the apparatus for evaluating a drug effect 100 using the model cell chip of the present invention with specific measurements is described below.

FIGS. 3(a), (b), (c) and (d) are graphs showing signals relating to the measurement of cell potential in the first embodiment of the present invention. The horizontal axis in each graph represents time and the vertical axis shows the cell potential obtained between the microelectrode 2 and the reference electrode $2_C$. FIG. 3(a) is the cell potential from the pulse of the cell population $CH_G$ of cardiomyocytes. In this case, shown is the potential between leading line $2'_G$ from the electrode, on which a single cardiomyocyte of the cell population $CH_G$ shown in FIG. 1 is arranged, and leading line $2'_C$ from the reference electrode $2_C$. As shown in the figure, this potential illustrates that the pulse is stable and can function as a pacemaker. FIG. 3(b) is a cell potential from the pulse of a target cell in a normal state wherein the liquid culture medium does not contain a drug. In this case the target cell for measurement is the hERG-expressing cell of cell holder $CH_1$. The figure shows the potential measured between the leading line $T_1$ from the electrode, on which the hERG-expressing cell $10_1$ is arranged, and the leading line $2'_C$ from the reference electrode $2_C$. As one can clearly see by comparison with the waveform of FIG. 3(a), a waveform is observed that is primarily the change in cell potential associated with the influx and efflux of only the $K^+$ ion component in the hERG-expressing cell $10_1$. In contrast, FIG. 3(c) is a cell potential that is primarily the change in cell potential associated with the influx and efflux of only the $K^+$ ion component in the target cell hERG-expressing cell $10_1$ in a state wherein the liquid culture medium contains a drug. Here the drug is detected by a state of decreased signal intensity because the drug has decreased the influx and efflux of only the $K^+$ ion component of the hERG-expressing cell $10_1$. FIG. 3(d) is the cell potential that is primarily the change in cell potential associated with the influx and efflux of only the $K^+$ ion component in the target cell hERG-expressing cell $10_1$ in a state wherein the drug contained in the liquid culture medium is included. Here the drug is detected by a state of decreased signal intensity because the drug has decreased the influx and efflux of only the $K^+$ ion component of the hERG-expressing cell $10_1$. In other words, the toxicity of a drug toward hERG-expressing cells can be evaluated as a decrease in signal intensity.

In the first embodiment, the substrate 1 and the electrode 2 were constructed using an optically transparent material, and they have not been specifically described, but this enables the combined use of an observation of the state of cell pulsation using an optical microscope. Thus, evaluation of the effect of the drug is possible from many aspects rather than merely from pulse potential. Conversely, when observations with an optical microscope are not to be performed, it is not necessary to construct the substrate 1 and electrode 2 using an optically transparent material.

Figure 4:
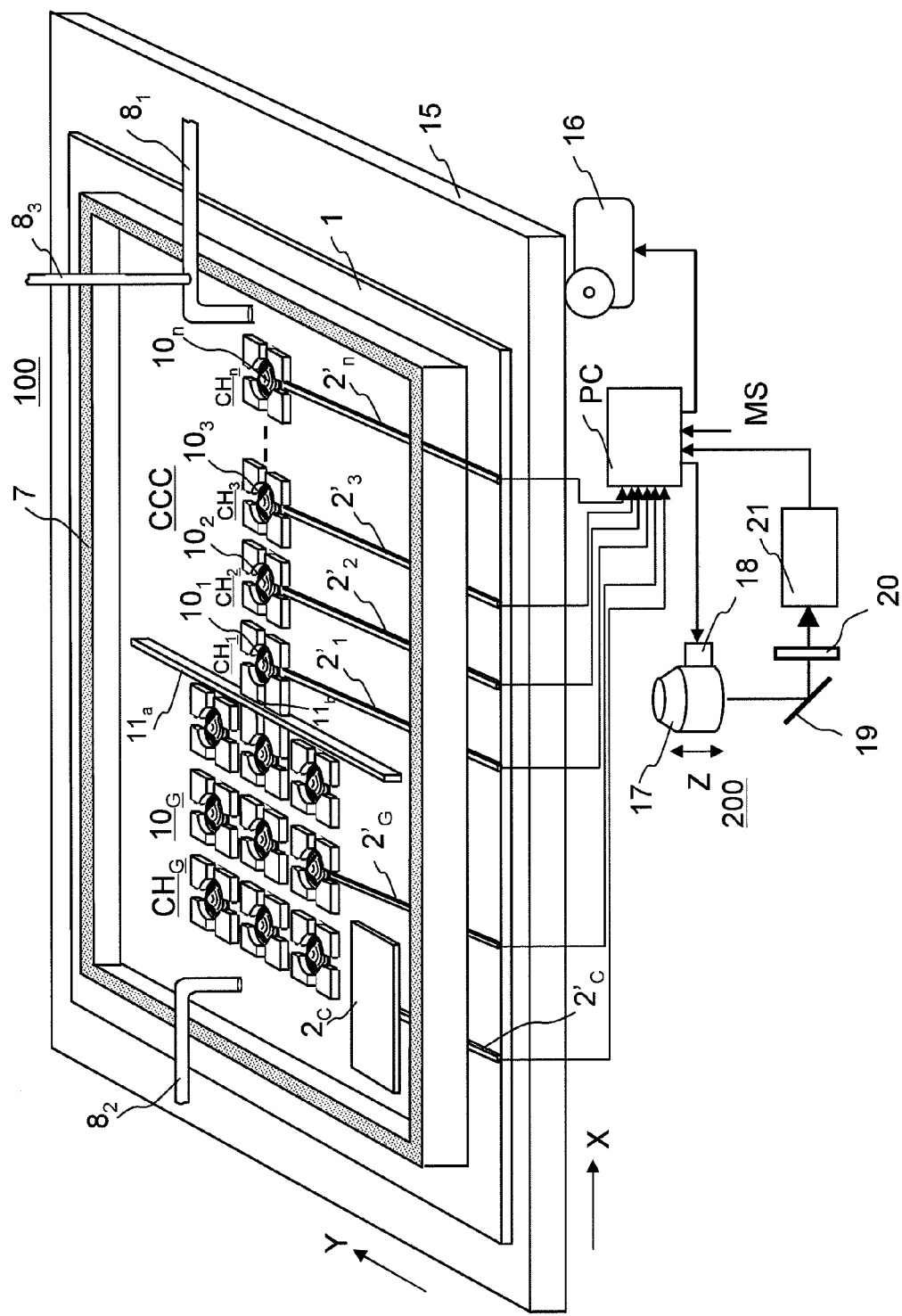
FIG. 4 is a perspective view schematically illustrating one example of the structure of the myocardial toxicity test apparatus as in the second embodiment of the present invention.
Figure 5:
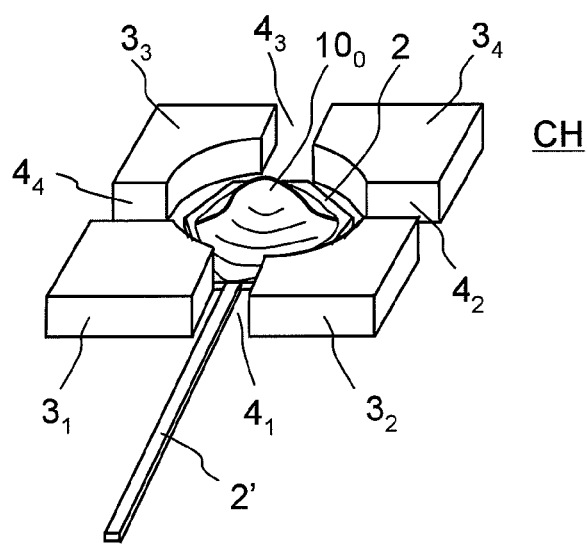
FIG. 5 is a perspective view schematically illustrating one example of the cell holder CH of the myocardial toxicity test apparatus shown in FIG. 4.
Figure 6:
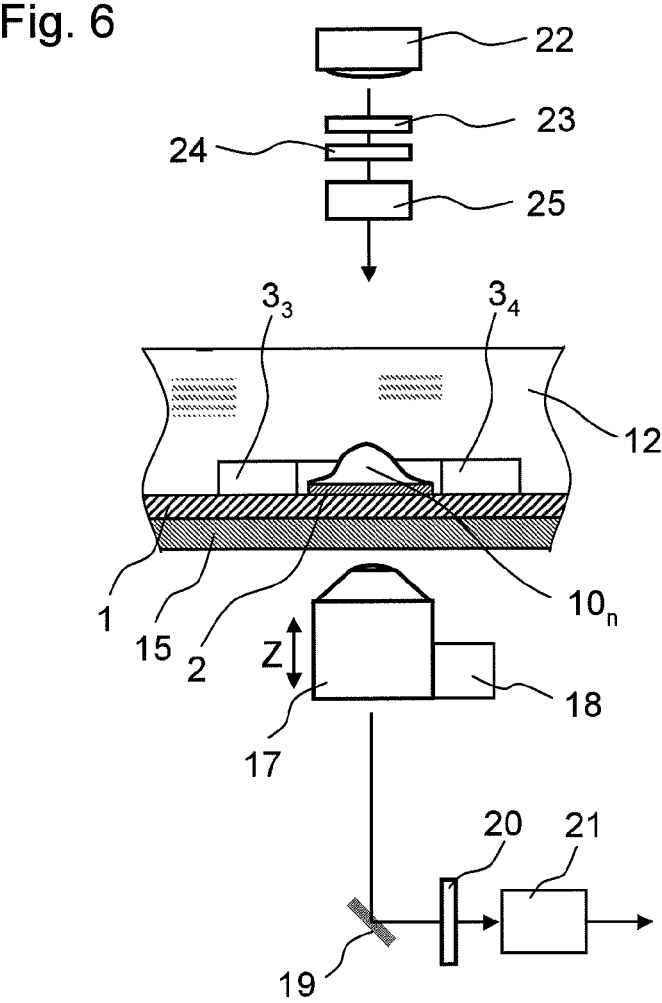
FIG. 6 is a diagram explaining the optical system for optically detecting a cell held in a cell holder CH of the myocardial toxicity test apparatus shown in FIG. 4.

FIG. 4 is a perspective view schematically illustrating one example of the structure of the myocardial toxicity test apparatus relating to the second embodiment of the present invention. FIG. 5 is a perspective view schematically illustrating one example of the cell holder CH of the myocardial toxicity test apparatus shown in FIG. 4. FIG. 6 is a diagram explaining the optical system for optically detecting a cell held in a cell holder CH of the myocardial toxicity test apparatus shown in FIG. 4.

In the figure, 100 is the myocardial toxicity test apparatus using a model cell chip, and the structure constitutes mainly parts configured on a transparent substrate 1. The transparent substrate 1 is an optically transparent material, for example a glass substrate or silicon substrate. The microelectrode 2 is, for example, an ITO transparent electrode, and is configured on the transparent substrate 1. The leading line 2' is a line for the microelectrode 2. Walls are formed of agarose gel $3_1$, $3_2$, $3_3$, and $3_4$ configured around the microelectrode 2 with gaps $4_1$, $4_2$, $4_3$, and $4_4$. The agarose gel walls $3_1$, $3_2$, $3_3$, and $3_4$ are cut out in the center to form a hollow space constituting a cell holding member. As needed, a microelectrode 2 is configured on the transparent substrate 1 in the hollow space constituting a cell holder formed by the agarose gel walls $3_1$, $3_2$, $3_3$, and $3_4$. The cell holder can hold a single cell 10 regardless of the presence or absence of a microelectrode 2. In FIG. 5, a microelectrode 2 is configured in the hollow space constituting the cell holding member formed by the agarose gel walls $3_1$, $3_2$, $3_3$, and $3_4$ on the transparent substrate 1, and a cardiomyocyte $10_0$ is arranged on the microelectrode 2. The figure shows a leading line 2' connected to and leading from the microelectrode 2. A substance such as collagen can be applied to the cell holding surface to facilitate cell adhesion when a cell is arranged directly on the cell holding surface of the microelectrode 2 or on the transparent substrate 1 provided without a microelectrode 2. With respect to the cell in the cell holding member formed by the agarose gel walls $3_1$, $3_2$, $3_3$, and $3_4$, because the agarose gel is a non-adhesive surface to cells, the cell 10 cannot climb over the wall and migrate even if the height of the agarose gel walls $3_1$, $3_2$, $3_3$, and $3_4$ is about the same as the height of the cell. In addition, because the gaps $4_1$, $4_2$, $4_3$, and $4_4$ around the cell holding member formed by cutting out the center of the agarose gel walls $3_1$, $3_2$, $3_3$, and $3_4$ are smaller than the size of a cell, the cell 10 cannot slip through the gaps $4_1$, $4_2$, $4_3$, and $4_4$.

In FIG. 4 each of the cell holders $CH_1$, $CH_2$, $CH_3$ and $CH_n$ holds a single cardiomyocyte or fibroblast $10_1$, $10_2$, $10_3$, and $10_n$ in the cell holding member thereof, and although it is not clearly shown in the figure, each is provided with a microelectrode 2, and a leading line $T_1$, $2'_2$, $2'_3$, and $2'_n$ leads therefrom. These cardiomyocytes and fibroblasts are arranged in tandem and constitute the cell communication channel CCC. In this case, n represents a number such as 20, for example. The distribution of these 20 cardiomyocytes and fibroblasts arranged in tandem can be random, but it is preferable for the cells of cell holder $CH_1$ and $CH_{20}$ to be cardiomyocytes. At the left edge of the cell communication channel CCC, there is a cardiomyocyte population holding area comprising a cell population $10_G$, wherein a 3×3 array of cell holders $CH_G$ is formed, and a cardiomyocyte 10 is held in each cell holder CH. This cell population $10_G$ functions as a pacemaker producing a stable pulse. In this cell population $10_G$, a microelectrode 2 is provided only to a single cell holder CH of the cell population $10_G$, and a leading line $2'_G$ leads therefrom. The cell holder CH in the center of the right side of the cell population $10_G$ is configured to lie opposite to cell holder $CH_1$ of the cell communication channel CCC. A barrier $11_a$ is provided between the right side of the cell population $10_G$ and the left edge of the cell communication channel CCC. A small opening $11_b$ is formed in the bottom part of the center of the barrier $11_a$. The cell holder CH in the center of the right side of the cell population $10_G$ and the cell holder $CH_1$ of the cell communication channel CCC lie opposite each other on both sides of the opening $11_b$, and they are constructed to allow physical contact and intercellular interaction between the cells held in each via the gaps 4 in the perimeter of the cell holding member of each. A reference electrode $2_C$ is provided at the bottom of the cell population $10_G$ and a leading line $2'_C$ leads therefrom.

Wall 7 encloses the cell population $10_G$, the cell communication channel CCC, and the reference electrode $2_C$, thereby surrounding the perimeter. Pipes $8_1$ and $8_2$ supply liquid culture medium to the area inside the wall 7 and withdraw liquid culture medium from the area inside the wall 7. In the example of this figure, the liquid culture medium is supplied via pipe $8_1$ that extends nearly to the bottom surface of the substrate 1, and the liquid culture medium is withdrawn via pipe $8_2$ that extends nearly to the bottom surface of the substrate 1. Pipe $8_3$ is connected near the liquid culture medium outlet of pipe $8_1$ that supplies liquid culture medium, and the drug acting on the cells is supplied via pipe $8_3$. Thus, the cell 10 is held stably on top of the microelectrode 2 while it is exposed to liquid culture medium supplied to the area inside the wall 7 via pipe $8_1$. When it is not necessary to expose the cells to liquid culture medium, the liquid culture medium can be withdrawn from the area inside the wall 7 via pipe $8_2$. In addition, when replacing the liquid culture medium with fresh medium, the fresh medium can be supplied either during or after withdrawal of the old culture medium. On the other hand, when exposing the cells to a drug, the drug acting on the cells can be added to the liquid culture medium via pipe $8_3$, and the liquid culture medium can then be supplied via pipe $8_1$ while withdrawing liquid culture medium via pipe $8_2$. At this time when liquid culture medium containing the drug is supplied to the area inside the wall 7 via pipe $8_1$, the extent of the effect of the drug on the cells of the cell population $10_G$ will be less than the effect of the drug on the cell of the cell communication channel CCC because the barrier $11_a$ has been provided between the cell population $10_G$ and the cell communication channel CCC. In other words, when liquid culture medium containing the drug is supplied via pipe $8_1$, the liquid culture medium flows through the gaps between the wall 7 and both sides of the barrier $11_a$, and it also flows over the top of the barrier $11_a$ and is supplied to the cell population $10_G$, so the drug also affects the cells of the cell population $10_G$. However, because the effect on those cells is indirect in comparison with the effect on the cell of the cell communication channel CCC, it is not great enough to affect their function as a pacemaker. The features and distribution of pipes $8_1$, $8_2$, and $8_3$ can be changed as desired in accordance with the method of measurement. For example, pipes $8_1$ and $8_3$ can be separated, or pipe $8_2$ can be omitted and pipe $8_1$ can be used for both supply and withdrawal.

In the figure, PC represents a personal computer, and it measures and records the cell potential between the leading line 2' of the microelectrode 2 of the cell holder CH and the leading line 2' of the reference electrode $2_C$. A manipulation signal Ms from an operator is sent to the personal computer 9.

The myocardial toxicity test apparatus 100 enables observation by an optical system of the pulsation of an arbitrary cell 10 in the cell communication channel CCC that is mounted on the X-Y stage 15 of the optical observation apparatus 200. The X-Y stage 15 is optically transparent and can be moved to an arbitrary position by an X-Y drive apparatus 16 in response to a signal from the personal computer PC in accordance with a manipulation signal Ms from an operator. An example of the observation of the state of pulsation of a cell $10_n$ in the cell communication channel CCC is shown in FIG. 6. In the figure, 12 represents liquid culture medium.

In the figure, 22 represents a light source for a phase contrast microscope or differential interference microscope, and generally a halogen lamp is used therefor. A bandpass filter 23 allows only light of a specific wavelength to pass through from the light source of a stereomicroscope such as a phase contrast microscope, etc. For example, in the observation of the cell $10_n$, damage to the cell $10_n$ can be avoided by using light of a narrow bandwidth near a wavelength of 700 nm. A shutter 24 has the function of blocking exposure to light when an image measurement is not being performed, such as when the X-Y stage 15 is being moved. A condenser 25 allows insertion of a phase contrast ring when a phase contrast observation is performed or a polarizer when a differential interference observation is performed. On the X-Y stage 15 is mounted a cell response measuring apparatus 100 formed on the substrate 1, and by moving the abovementioned X-Y stage 15 by the X-Y drive apparatus 16, it is possible to observe and measure an arbitrary position on the above-mentioned cell response measurement apparatus 100. The state of pulsation of the cell $10_n$ in the abovementioned cell response measurement apparatus 100 is observed through the objective lens 17. The focal position of the objective lens 17 can be moved in the Z-axis direction by a drive apparatus 18 in response to a signal from the personal computer PC. A magnification ratio of 40× or higher can be used for the objective lens 17. A phase contrast image or differential interference image of the cell $10_n$ can be observed by the objective lens 17 in accordance with the light transmitted from the light source 22. A phase contrast microscope image or differential interference microscope image only is observed by the camera 21 in accordance with a dichroic mirror 19 that reflects light of the same wavelength as that passing through the abovementioned bandpass filter 23 and bandpass filter 20. The image signal observed by the camera 21 is fed into the personal computer PC.

The sizes of the main structures of the myocardial toxicity test apparatus 100 illustrated in FIG. 4 are noted below. This example assumes a cell size of 10 µm in diameter. The size of the transparent substrate 1 is 100 mm×150 mm; the size of the microelectrode 2 is 8 µm×8 µm; the size of each of the agarose gel walls $3_1$, $3_2$, $3_3$, and $3_4$ is 20 µm×20 µm×10 µm (height); the width of the gaps $4_1$, $4_2$, $4_3$, and $4_4$ is 2 µm, the hollow space that is the cell holding member formed by the agarose gel walls $3_1$, $3_2$, $3_3$, and $3_4$ is a cylinder 12 µm in diameter; and the outside perimeter of the wall 7 is 5 mm×5 mm, and the height is also 5 mm. The height of the barrier $11_a$ is 1 mm. This case assumes that the microelectrode 2 is an 8 µm×8 µm square, but a round electrode with a 10 µm diameter to form the cell holding member constituted by the all four agarose gel walls $3_1$, $3_2$, $3_3$, and $3_4$, and the width of the gaps $4_1$, $4_2$, $4_3$, and $4_4$ can also be used.

A structural example of the cell response measuring apparatus 100 of the present invention with specific measurements is described below.

Figure 7:
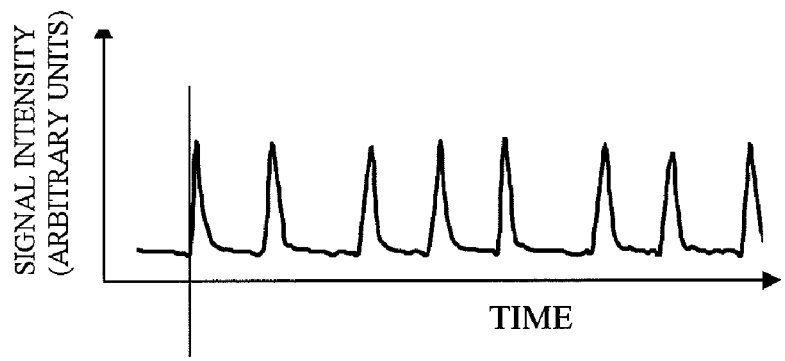
FIGS. 7(a), (b), and (c) are graphs showing signals relating to the measurement of cell potential. More specifically, (a) is the cell potential based on the pulse of a cell population $10_G$, (b) is a cell potential based on the pulsation of a target cell in the normal state wherein the liquid culture medium does not contain the drug, and (c) is the cell potential based on the pulse of a target cell in a state wherein the liquid culture medium contains the drug. The horizontal axis represents time, and the vertical axis represents cell potential obtained between the microelectrode 2 and the reference electrode $2_C$.
Figure 7:
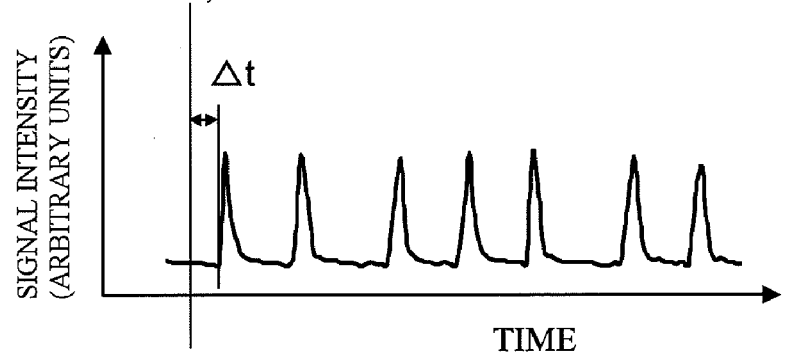
Figure 7:
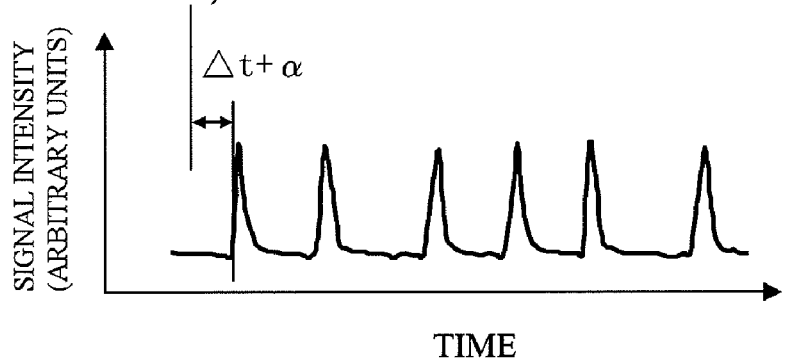

FIGS. 7(*a*), (*b*), and (*c*) are graphs showing signals relating to the measurement of cell potential. In each case, the horizontal axis represents time and the vertical axis represents cell potential obtained between the microelectrode 2 and the reference electrode $2_C$. FIG. 7(*a*) is the cell potential obtained from the pulsation of the cell population $10_G$. In this case, it is the potential between the leading line $2'_G$ from a single cell of the cell population $10_G$ and the leading line $T_C$ from the reference electrode $2_C$ shown in FIG. 4. As illustrated in the figure, it is clear that the pulse is stable and can function as a pacemaker. FIG. 7(*b*) is the cell potential based on the pulsation of a target cell in a normal state wherein the liquid culture medium does not contain the drug. Here the target cell to be measured is cell $10_n$ of the cell communication channel CCC, and the cell potential is measured between the leading line $2'_n$ from cell $10_n$ and the leading line $2'_C$ from the reference electrode $2_C$. As can be clearly seen from a comparison with the waveform of FIG. 7(*a*), there is time lag by time Δt which is required for the transmission of the pulse based on cell 10 of the cell communication channel CCC. In contrast, FIG. 7(*c*) is the cell potential based on the pulsation of the target cell in a state wherein the liquid culture medium contains the drug. In this case as well, cell $10_n$ of the cell communication channel CCC is designated as the target cell for measurement to make the comparison with FIG. 7(*b*) very clear. As one can clearly see from the comparison of waveforms of FIGS. 7(*a*) and 7(*b*), not only the time lag Δt, the time required for the transmission of the pulse based on cell 10 of the cell communication chamber CCC, but an additional time lag Δt+α was observed. This means that the sodium ion inhibition due to the action of the drug on the cell of the cell communication channel CCC is expressed as an increase +α in the time lag. In other words, the toxicity of the drug toward cardiomyocytes can be evaluated as sodium ion inhibition.

Figure 8:
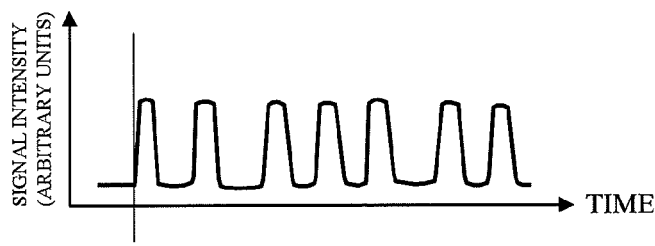
FIGS. 8(a), (b), and (c) are graphs showing signals related to results of changes in volume accompanied by cell pulsation measured by the optical system. More specifically, (a) is the change in volume accompanied by the pulsation of a cell of the cell population $10_G$. In the top row, (b) shows the change in volume accompanied by the pulsation of a target cell in the normal state wherein the liquid culture medium does not contain the drug, and in the bottom row it shows the waveform when this is processed as a time derivative for evaluating the change in volume as an electrical signal. (c) is an explanatory diagram for evaluating the change in volume accompanied by the pulsation of a target cell in a state wherein the liquid culture medium contains the drug, and it is shown in a form with an expanded time axis relative to FIGS. 8(a) and (b)
Figure 8:
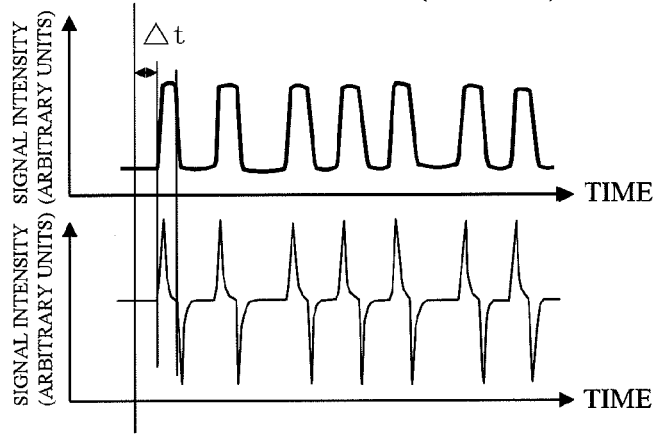
Figure 8:
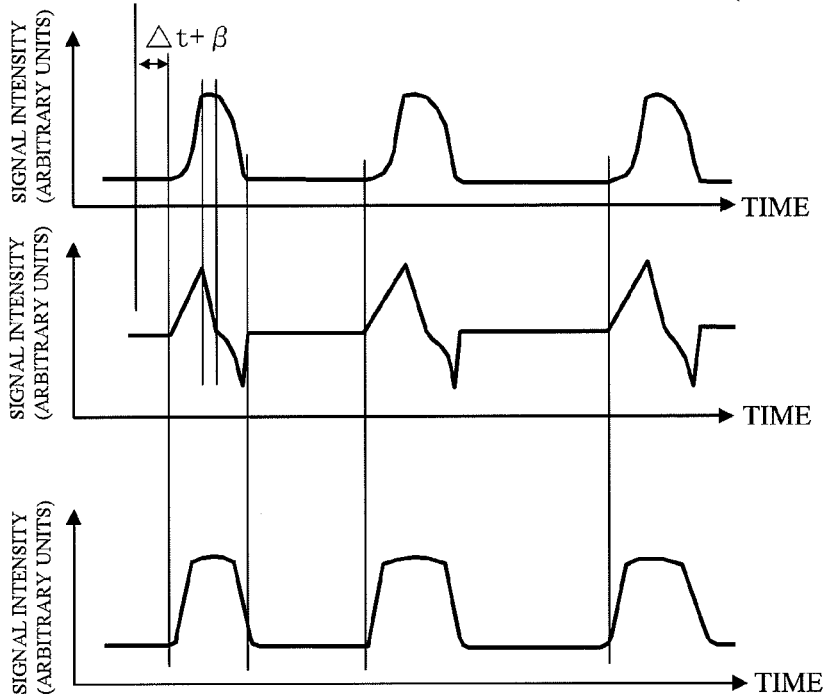

FIGS. 8(*a*), (*b*), and (*c*) are graphs showing signals related to results of changes in volume associated with cell pulsation measured by the optical system. FIG. 8(*a*) is the change in volume associated with the pulsation of the cell in cell population $10_G$. The pulsation of a single cell of cell population $10_G$ was detected optically in the manner shown in FIG. 6. The contraction and expansion associated with the pulsation of a cell are considered to be changes that appear in the state of pulsation. The cycle of the waveform is the same as the cycle of changes in cell potential associated with the pulsation illustrated in FIG. 7(*a*). In the top row FIG. 8(*b*) shows the change in volume accompanied by the pulsation of a target cell in the normal state wherein the liquid culture medium does not contain the drug, and in the bottom row it shows the waveform when this is processed as a time derivative for evaluating the change in volume as an electrical signal. In this case as well, cell $10_n$ of the cell communication channel CCC was designated as the target cell for measurement, and the pulsation of cell $10_n$ was detected optically in the manner shown in FIG. 6. As can be clearly seen from a comparison with the waveform of FIG. 8(*a*), there is time lag by time Δt which is required for the transmission of the pulse based on cell 10 of the cell communication channel CCC. In contrast, FIG. 8(*c*) is an explanatory figure for evaluating the change in volume accompanied by pulsation of a target cell in a state wherein the liquid culture medium does not contain a drug, and relative to FIGS. 8(*a*) and 8(*b*), the time axis is expanded. The top row corresponds to the waveform of the top row of FIG. 8(*b*), and as one can clearly see from a comparison with the waveform of FIG. 8(*a*), only a time lag of β in addition to the time Δt required for the transmission of the pulse based on cell 10 of the cell communication channel CCC is observed. The effect of the drug on the change in volume accompanied by pulsation of the target cell is characteristic in that the slope of the change in volume is smaller than the amount of increase in the time lag. This can clearly be seen by making a comparison with the change in volume when the liquid culture medium contains no drug, which is shown as a reference waveform on the bottom row of FIG. 8(*c*). The center row of FIG. 8(*c*) shows a waveform when the waveform of the top row is processed as a time derivative for evaluation. As one can see by comparing this time derivative with that of the bottom row of FIG. 8(*b*), the peak value becomes smaller and the slope becomes gentler. This means that the myocardial contraction rate decreases due to the drug, and the cardiac output has decreased. In other words, the toxicity of the drug toward cardiomyocytes can be evaluated as a decrease in contraction rate.

Figure 9:
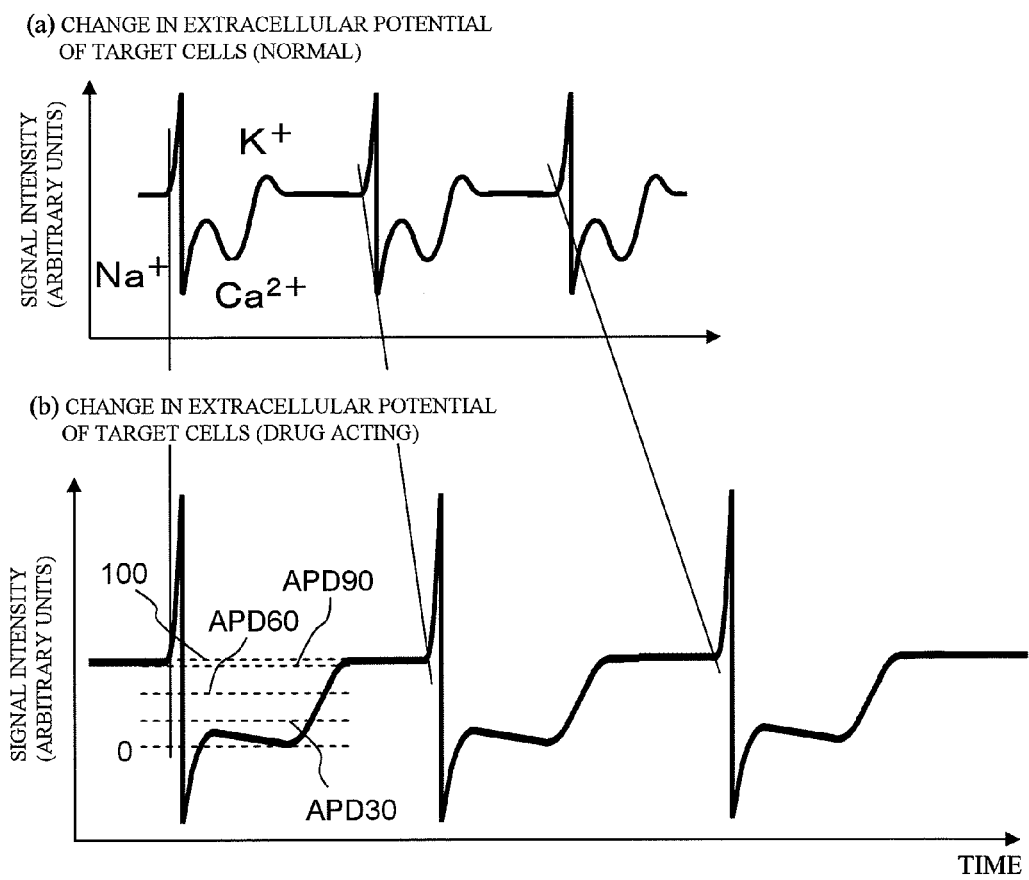
FIG. 9(a) is a diagram showing the change in cell potential accompanied by the influx and efflux of $Na^+$ ion, $Ca^{2+}$ ion, and $K^+$ ion components of the target cell in the normal state wherein the liquid culture medium does not contain the drug, and (b) is a diagram showing the change in cell potential accompanied by the influx and efflux of $Na^+$ ion, $Ca^{2+}$ ion, and $K^+$ ion components of the target cell in a state wherein the liquid culture medium contains the drug.

FIG. 9(*a*) is a diagram showing the change in cell potential accompanied by the influx and efflux of $Na^+$ ion, $Ca^{2+}$ ion, and $K^+$ ion components of the target cell in the normal state wherein the liquid culture medium does not contain the drug. FIG. 9(*b*) is a diagram showing the change in cell potential accompanied by the influx and efflux of $Na^+$ ion, $Ca^{2+}$ ion, and $K^+$ ion components of the target cell in a state wherein the liquid culture medium contains the drug. As one can immediately see by comparing FIGS. 9(*a*) and 9(*b*), a QT prolongation has appeared, and the waveform is expanded in the direction of the time axis. In addition, the waveform is greatly deformed accompanied by the influx and efflux of $K^+$ ions. To evaluate this as an electrical signal, the duration of the action potential at 30%, 60%, and 90% relative to values between 0 and 100, which are shown by the broken lines in the figure, is designated as APD30, APD60, and APD90, respectively. Here, the term APD is an expression taken from the first letters of the term Action Potential Duration. By evaluating the amplitude and ratio of these values, the effect of the drug on the influx and efflux of the $Na^+$ ion, $Ca^{2+}$ ion, and $K^+$ ion components can be evaluated.

In a typical example of the second embodiment of the present invention, a pulsating pacemaker cell population is configured on a transparent substrate, and then a myocardial pulsating cell is configured at a suitable distance therefrom. A suitable number of fibroblasts are configured and connected in between to construct a cell network. The myocardial pulsating cell and the fibroblasts constituting the network are each configured on transparent electrodes provided on the transparent substrate. This cell network can be observed optically. The cells constituting the network are exposed to the flow of a liquid containing a drug acting on the cells. The inhibition of $Na^+$ ions is evaluated by capturing the difference between the normal time lag in pulse propagation from the first myocardial pulsating cell of the network to the last myocardial pulsating cell and the time lag in pulse propagation when the drug is acting on the cells using the electrical signals obtained from the electrodes. The contraction rate when the drug is acting is detected by optically capturing a single pulsation of a myocardial pulsating cell in the network and detecting the change in volume of thereof, and the cardiac output is evaluated then thereby. By electrically capturing a single pulsation of a myocardial pulsating cell in the network, the influx and efflux of the $Na^+$ ion, $Ca^{2+}$ ion, and $K^+$ ion components can be calculated, and the QT prolongation resulting from the drug can be evaluated.

INDUSTRIAL APPLICABILITY

In accordance with the present invention, the effect of a drug, i.e., the drug effect, on an hERG-expressing cell, can be evaluated equivalently in vitro based on a pulse obtained using a cell population as a pacemaker.

In accordance with the present invention, the response to the transmission of a pulse by a cell and the effect of a drug, i.e., the myocardial toxicity of a drug, in relation to the same can be evaluated equivalently in vitro using a cell communication channel CCC wherein cardiomyocytes and fibroblasts are arranged in tandem based on a pulse using a cell population as a pacemaker.

The invention claimed is:

1. A myocardial toxicity test chip, comprising:
a transparent substrate;
a cardiomyocyte population holding area arranged on the transparent substrate and having a first plurality of cell holders ($CH_G$) holding stably pulsating cardiomyocytes;
a cell communication channel formed by a second plurality of cell holders ($CH_n$) arranged in tandem in which the $CH_n$ holds cardiomyocytes or fibroblasts, wherein the cardiomyocyte population holding area adjoins the cell communication channel at a first cell holder ($CH_1$) of the $CH_n$;
a liquid culture medium area defined by a surface of the transparent substrate and a wall formed around the perimeter of the cardiomyocyte population holding area and the cell communication channel;
a microelectrode placed in one cell holder ($CH_G$) in the cardiomyocyte population holding area on the transparent substrate;
a further microelectrode placed in each of the second plurality of cell holders ($CH_n$) of the cell communication channel on the transparent substrate;
a reference electrode placed in the liquid culture medium area; and
a leading line connected to the microelectrode in the cardiomyocyte population holding area, a leading line connected to the plurality of the further microelectrodes, and a leading line connected to the reference electrode.

2. The myocardial toxicity test chip according to claim 1, wherein each of the $CH_G$ cell holders and the $CH_n$ cell holders are each a space on the transparent substrate and enclosed by walls that are non-adhesive to cells in each of the $CH_G$ cell holders and the $CH_n$ cell holders, and the walls have one or more gaps too narrow for the cell to pass therethrough.

3. The myocardial toxicity test chip according to claim 1, wherein a barrier is provided between the cardiomyocyte population holding area and the cell communication channel in order to impede the flow of the cell culture medium, the barrier having an opening for making a cell held in one of the plurality of cell holders ($CH_G$) in the cardiomyocyte population holding area communicate with a cell in the cell holder ($CH_n$) on the end of the cell communication channel.

4. A myocardial toxicity test apparatus, comprising:
a transparent substrate;
a cardiomyocyte population holding area arranged on the transparent substrate and having a first plurality of cell holders ($CH_G$) holding stably pulsating cardiomyocytes;
a cell communication channel formed by a second plurality of cell holders ($CH_n$) arranged in tandem in which the $CH_n$ holds cardiomyocytes or fibroblasts, wherein the cardiomyocyte population holding area adjoins the cell communication channel at a first cell holder ($CH_1$) of the $CH_n$;
a liquid medium area defined by a surface of the transparent substrate and a wall formed around the perimeter of the cardiomyocyte population holding area and the cell communication channel;
a first pipe to supply liquid culture medium to the liquid medium area and a second pipe to withdraw liquid culture medium from the liquid medium area;
a third pipe to supply a drug to the liquid culture medium;
a microelectrode placed in one cell holder ($CH_G$) in the cardiomyocyte population holding area on the transparent substrate;
a microelectrode placed in each of the second plurality of cell holders ($CH_n$) of the cell communication channel on the transparent substrate;
a reference electrode placed in the liquid medium area;
a device to measure and record a change in cell potential of cells arranged on the microelectrodes from a leading line connected to each of the microelectrodes and a leading line connected to the reference electrode; and
a device to optically measure a state of cells arranged on the transparent substrate.

5. The myocardial toxicity test apparatus according to claim 4, wherein each of the $CH_G$ cell holders and the $CH_n$ cell holders are each a space on the transparent substrate and enclosed by walls that are non-adhesive to cells in each of the $CH_G$ cell holders and the $CH_n$ cell holders, and the walls have one or more gaps too narrow for the cell to pass therethrough.

6. The myocardial toxicity test apparatus according to claim 4, wherein a barrier is provided between the cardiomyocyte population holding area and the cell communication channel in order to impede the flow of the cell culture medium, the barrier having an opening for making a cell held in one of the plurality of cell holders ($CH_G$) in the cardiomyocyte population holding area communicate with a cell in the cell holder ($CH_n$) on the end of the cell communication channel.

7. A myocardial toxicity test apparatus, comprising:
   a transparent substrate;
   a cardiomyocyte population holding area arranged on the transparent substrate and having a first plurality of cell holders ($CH_G$) holding stably pulsating cardiomyocytes;
   a cell communication channel formed by a second plurality of cell holders ($CH_n$) arranged in tandem in which the $CH_n$ holds cardiomyocytes or fibroblasts, wherein the cardiomyocyte population holding area adjoins the cell communication channel at a first cell holder ($CH_1$) of the $CH_n$;
   an liquid medium area defined by a surface of the transparent substrate and a wall formed around the perimeter of the cardiomyocyte population holding area and the cell communication channel;
   a first pipe to supply liquid culture medium supply to the liquid medium area and a second pipe to withdraw the liquid culture medium from the liquid medium area;
   a third pipe to supply a drug to the liquid culture medium;
   a microelectrode placed in one cell holder ($CH_G$) of the cardiomyocyte population holding area on the transparent substrate;
   a microelectrode placed in each of the second plurality of cell holders ($CH_n$) of the cell communication channel on the transparent substrate;
   a reference electrode placed in the liquid medium area;
   a device to measure and record a change in cell potential of cells arranged on the microelectrodes from a leading line connected to each of the microelectrodes and a leading line connected to the reference electrode;
   a stage which can be moved in the X-Y direction, and on which the transparent substrate is arranged; and
   a device to optically measure the state of cells on the transparent substrate arranged on the stage.

8. A myocardial toxicity test method, wherein using the myocardial toxicity test apparatus according to any of claims 4 to 7, the myocardial toxicity of a drug is tested by evaluating whether or not there is a time lag in the speed at which the pulse generated by the cell population is transmitted via the cell communication channel when a drug acting on the cells has been added to the liquid culture medium.

\* \* \* \* \*